(12) United States Patent
Mueller

(10) Patent No.: US 11,524,806 B2
(45) Date of Patent: Dec. 13, 2022

(54) METHOD AND DEVICE FOR STERILIZING CLOSURE ELEMENTS FOR PACKAGING CONTAINERS, AND USE THEREOF

(71) Applicant: Syntegon Technology GmbH, Waiblingen (DE)

(72) Inventor: Peter Mueller, Mutlangen (DE)

(73) Assignee: SYNTEGON TECHNOLOGY GMBH, Waiblingen (DE)

( * ) Notice: Subject to any disclaimer, the term of this patent is extended or adjusted under 35 U.S.C. 154(b) by 443 days.

(21) Appl. No.: 16/697,707

(22) Filed: Nov. 27, 2019

(65) Prior Publication Data
US 2020/0165021 A1  May 28, 2020

(30) Foreign Application Priority Data
Nov. 28, 2018 (DE) .......................... 102018220486.1

(51) Int. Cl.
| | |
|---|---|
| B65B 55/10 | (2006.01) |
| B65B 55/02 | (2006.01) |
| B65B 55/06 | (2006.01) |
| B65B 43/46 | (2006.01) |
| B65B 43/50 | (2006.01) |
| A61L 2/06 | (2006.01) |
| A61L 2/20 | (2006.01) |

(52) U.S. Cl.
CPC ................ *B65B 55/10* (2013.01); *A61L 2/06* (2013.01); *A61L 2/208* (2013.01); *B65B 43/46* (2013.01); *B65B 43/50* (2013.01); *B65B 55/027* (2013.01); *B65B 55/06* (2013.01); *A61L 2202/11* (2013.01); *A61L 2202/122* (2013.01); *A61L 2202/15* (2013.01); *A61L 2202/23* (2013.01)

(58) Field of Classification Search
CPC ....... B65B 43/46; B65B 43/50; B65B 55/027; A61L 2202/122
USPC .............................................. 422/302; 53/426
See application file for complete search history.

(56) References Cited

U.S. PATENT DOCUMENTS 4,981,649 A * 1/1991 Shibauchi ............. B65B 7/2807
53/167
5,084,243 A * 1/1992 Wijts ........................ A61L 2/07
422/26

(Continued)

FOREIGN PATENT DOCUMENTS

| DE | 19851654 A1 | 5/2000 |
|---|---|---|
| DE | 102017200366 | 7/2018 |
| DE | 102017104153 A1 | 5/2021 |

OTHER PUBLICATIONS

French Patent Office Search Report and Written Opinion for Application No. 1912995 dated Mar. 29, 2022 (13 pages including English translation).

*Primary Examiner* — Robert F Long
*Assistant Examiner* — Xavier A Madison
(74) *Attorney, Agent, or Firm* — Michael Best & Friedrich LLP

(57) ABSTRACT

A method for sterilizing closure elements (3) for packaging containers (1), wherein the closure elements (3) are collected individually by a holding mechanism (25) in the region of a sterile chamber (12) and are placed onto an opening (4) of a filled packaging container (1) and connected to the latter, and wherein the closure elements (3), while being conveyed inside the sterile chamber (12), are treated by means of at least one sterilizing medium (6, 7, 52) during a sterilizing process.

13 Claims, 3 Drawing Sheets

(56) References Cited

U.S. PATENT DOCUMENTS

| | | | | |
|---|---|---|---|---|
| 6,056,918 A | * | 5/2000 | Palaniappan | B65B 55/10 |
| | | | | 53/565 |
| 6,341,472 B1 | * | 1/2002 | Schroeder | B67C 7/0073 |
| | | | | 53/317 |
| 7,412,811 B2 | * | 8/2008 | Marcus | B65B 31/043 |
| | | | | 422/302 |
| 8,834,808 B2 | | 9/2014 | Drenguis | |
| 2001/0046464 A1 | * | 11/2001 | Mykkanen | A61L 2/18 |
| | | | | 422/302 |
| 2009/0317295 A1 | * | 12/2009 | Yonesu | A61L 2/14 |
| | | | | 422/186.21 |
| 2011/0016829 A1 | * | 1/2011 | Drenguis | B65B 55/08 |
| | | | | 53/167 |

* cited by examiner

METHOD AND DEVICE FOR STERILIZING CLOSURE ELEMENTS FOR PACKAGING CONTAINERS, AND USE THEREOF

BACKGROUND OF THE INVENTION

The invention relates to a method for sterilizing closure elements for packaging containers, as is used for example in the region of a filling installation for filling and closing packaging containers that are used for yoghurt or similar food. The invention further relates to a device for carrying out in particular the method according to the invention, and to the use of a corresponding method and device in the field concerned with filling installations for foods.

A method for sterilizing closure elements for packaging containers, is known from DE 10 2017 200 366 A1 from the applicant. In the known method, lid-shaped closure elements are withdrawn by means of suction cups from a stack of closure elements in the region of a closure module that has a sterile chamber, and they are placed onto filled packaging containers and connected to the latter, in particular by sealing. During the conveying of the closure elements from the stack of closure elements to the openings of the packaging containers, the closure elements are sterilized by means of at least one sterilizing medium. Said document does not provide any details of how the surfaces of the closure elements are sterilized.

SUMMARY OF THE INVENTION

The method according to the invention, for sterilizing closure elements for packaging containers, has the advantage that all the surfaces of the closure elements can be sterilized or come into operative connection with at least one sterilizing medium. In particular, the at least one sterilizing medium also treats those regions of the surfaces of the closure elements which, during the conveying of the closure elements, are in holding contact with the holding mechanisms such that the sterilizing medium cannot act there on the closure elements, since the region is covered or protected by the holding mechanism. The complete sterilization of the closure elements, which is thereby made possible, thus satisfies strict sterilization demands inside the sterile chamber, thereby permitting a filling and closing process that is particularly reliable from the point of view of food technology, ensuring in particular that no germs or similar can come into contact with the packaged food or the like.

To achieve the stated advantages, provision is made in the method according to the invention that the holding mechanism for the closure elements holds the closure elements successively at different locations of the closure element during the sterilization, in such a way that during the sterilizing process all the surfaces of the closure element come temporarily into operative connection with the at least one sterilizing medium. In other words, since the holding mechanism, in the regions in which it holds the closure elements, is temporarily freed or removed from them, it is possible that, in these regions too, the sterilizing medium comes into contact or operative connection with the closure elements.

With a view to optimized sterilization of the closure elements, provision is made that the sterilization of the closure elements comprises a first phase in which hot air acts as sterilizing medium on the closure elements, a second phase in which vaporous sterilizing agent acts as sterilizing medium, in particular containing hydrogen peroxide, and a third phase in which the closure elements are dried with hot air, wherein at least during the first two phases the closure elements, in the region of all the surfaces, come into operative connection with the sterilizing medium.

The invention also comprises a device for sterilizing closure elements for packaging containers, wherein the device preferably operates by an above-described method according to the invention. The device comprises a holding mechanism for holding in each case one closure element in the region of a sterile chamber, and a sterilizing mechanism for at least one sterilizing medium for sterilizing the closure elements in the region of the sterile chamber. According to the invention, the device is characterized in that the holding mechanism has a plurality of holding elements for in each case one closure lid, which holding elements are alternately arranged temporarily out of contact with the closure element in order to allow the at least one sterilizing medium to act on a closure element. In other words, by virtue of the fact that the holding mechanism for each closure element has a plurality of holding elements, it is made possible that at least one holding element is arranged in contact or in operative connection with the closure element and, during this phase, the other regions of the closure element, which are arranged at a distance from the one or more other holding elements, can come into operative connection with the sterilizing medium.

In a development of the device according to the invention, provision is made that the holding elements are designed in the form of suction cups and that, in order to bring them out of contact with the closure element, a medium at an overpressure, preferably hot air, can act on the closure element through the suction cups. A structural configuration of this kind, particularly in connection with the usually flat or deformable lid-shaped closure elements, has the advantage that the suction cups can be arranged in a fixed position relative to the closure elements, and that, since hot air at an overpressure is applied or guided in the region of the suction cups, the closure element arrives at a distance from the suction cup. By virtue of the fact that preferably hot air is passed through the suction cups, this hot air serves at the same time to sterilize or pre-treat the closure elements before vaporous sterilizing medium or the like acts on them.

In order to hold a closure element as securely as possible and over a large surface area, provision is additionally made, in a further embodiment of the device according to the invention, that a plurality of holding elements assigned to a closure element are arranged simultaneously in holding contact with the closure element. This means that a closure element is held by at least two holding elements during each phase of its handling.

In a preferred arrangement of the holding mechanism, or of the holding elements, for achieving the highest possible output of the device, provision is made that the holding elements are arranged in a radially protruding manner on a conveying star rotatable about a rotation axle inside the sterile chamber. An arrangement of this kind has in particular the advantage that, during a continuous or else stepped rotation of the conveying star, the holding elements are able to collect individual closure elements which, during the further conveying upon rotation of the conveying star, can then be sterilized and finally can be brought into contact with the opening of the packaging container filled with food or similar.

In a development of the last proposal, provision is made that the holding elements are arranged radially movably with respect to the rotation axle of the conveying star in order to collect individual closure elements from a stack of closure elements and in order to place a closure element onto an opening of a filled packaging container.

Finally, the invention also relates to the use of an above-described device according to the invention and of an above-described method according to the invention for sterilizing deformable closure elements in the form of flat and/or molded or embossed closure lids in the region of a filling installation for foods such as yoghurt or the like.

Further advantages, features and details of the invention will become clear from the following description of preferred illustrative embodiments and by reference to the drawings.

DETAILED DESCRIPTION

In the following description of preferred embodiments of the invention, identical elements, or elements having an identical function, are provided with the same reference numbers in the figures.

Figure 1:
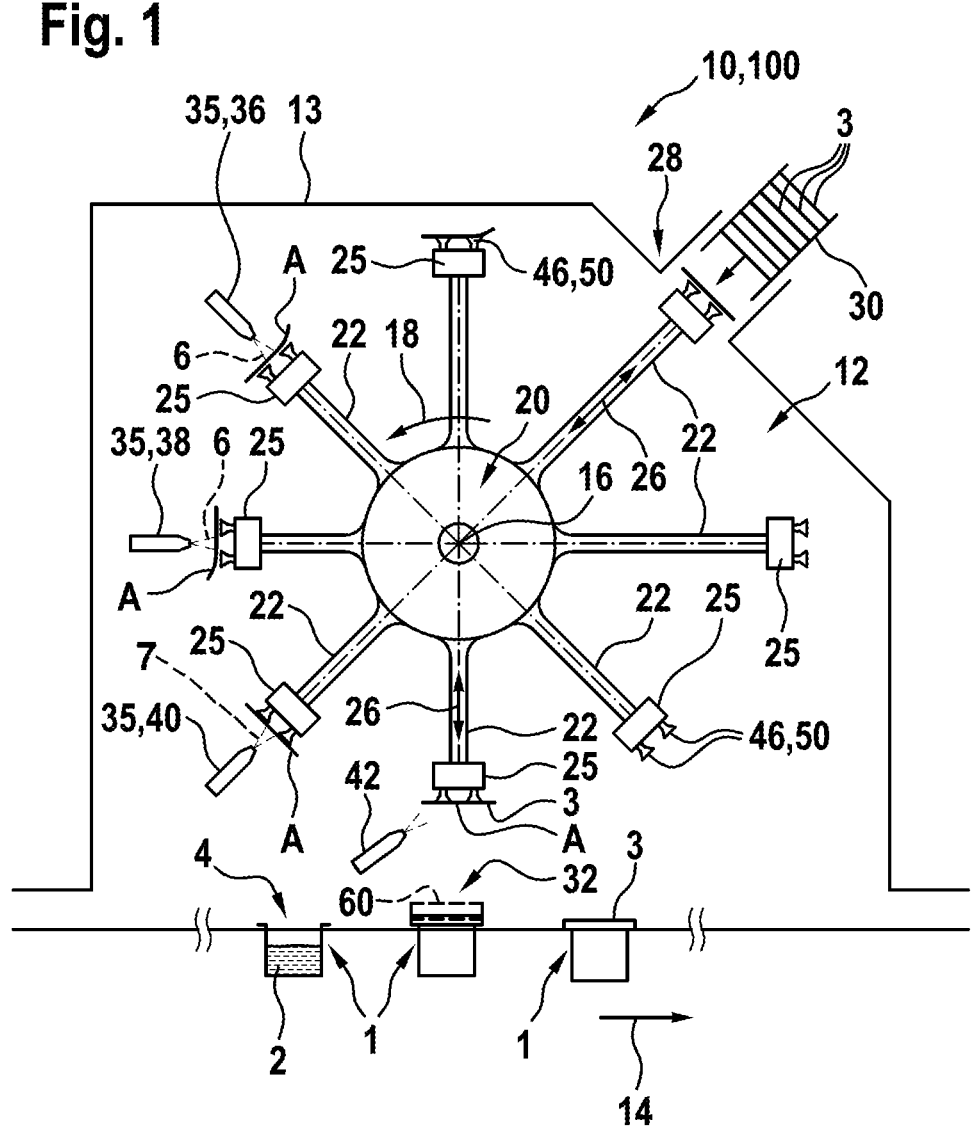
FIG. 1 shows a simplified view of a subregion of a filling installation for foods, in the region of a sterilizing and closing station.

FIG. 1 shows a subregion of a filling installation 100 for filling in particular thermoformed packaging containers 1 with a food 2 such as yoghurt or the like and for closing the packaging containers 1 with lid-shaped closure elements 3. The closure elements 3 are in particular deformable, flat blanks of aluminum or the like which for example have a thickness of a few tenths of a millimeter and which are placed onto the openings 4 of the filled packaging containers 1 and are connected to the latter, in particular by a heat sealing process or similar. For this purpose, the closure elements 3, on the side facing the opening 4 of the packaging containers 1, optionally have suitable coatings or similar, as is known per se from the prior art. Alternatively, the closure elements 3 can also be molded and/or embossed closure elements 3. The region of the filling installation 100 shown in FIG. 1 is the region of a device 10 for sterilizing the closure elements 3 and for placing the closure elements 3 onto the packaging containers 1.

The device 10 has a sterile chamber 12 with a housing wall 13, along the lower region of which the packaging containers 1, arranged at uniform distances from one another, are conveyed, preferably continuously, in the direction of the arrow 14 by means of a conveyor (not shown in detail). Inside the sterile chamber 12, the device 10 has a conveying star 20 which is rotatable counterclockwise about a rotation axle 16 in the direction of the arrow 18.

The conveying star 20 comprises, for example, eight holding arms 22 which are arranged at uniform angle distances about the rotation axle 16 and protrude radially from the rotation axle 16, and at the end regions of which, directed away from the rotation axle 16, a respective holding mechanism 25 is arranged for a closure element 3. Furthermore, the holding arms 22, or else the holding mechanisms 25 arranged on the holding arms 25, are arranged radially adjustably in the direction of the double arrow 26, such that it is possible to set different distances of the holding mechanisms 25 from the rotation axle 16.

In the region of a docking station 28 (not shown in detail) of the sterile chamber 12, a magazine 30 with a multiplicity of closure elements 3 stacked on top of each other can be docked onto the sterile chamber 12 in a manner sealed off from the external environment.

In the conveying path of the closure elements 3 between the region of the docking station 28 and a transfer region 32 where the closure elements 3 are transferred to the packaging containers 1, a sterilizing mechanism 35 with a plurality of different elements or mechanisms is arranged inside the sterile chamber 12. It will be seen in particular that there are, for example, two blower nozzles 36, 38 for blowing hot air 6 onto the undersides A of the closure elements 3 facing toward the food 2 in the packaging container 1. In the further conveying path of the closure elements 3 inside the sterile chamber 12, the sterilizing mechanism 35 additionally comprises at least one sterilizing nozzle 40 by which an in particular vaporous sterilizing agent 7, which preferably contains hydrogen peroxide, is applied or deposited onto the closure lids 3. Both the underside A and also the top side B of the closure elements 3 is treated or sterilized with the sterilizing agent 7 by means of the at least one sterilizing nozzle 40. The at least one sterilizing nozzle 40 is followed in turn by at least one hot-air nozzle 42 for final drying of the closure elements 3.

Figure 2:
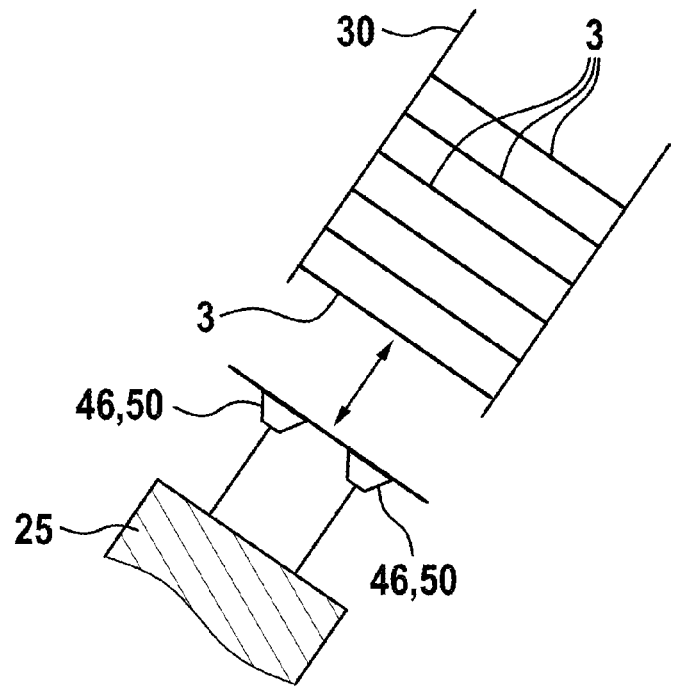
FIG. 2 shows a detail of the sterilizing and closing station according to FIG. 1, in the region of a stack of closure elements.
Figure 3:
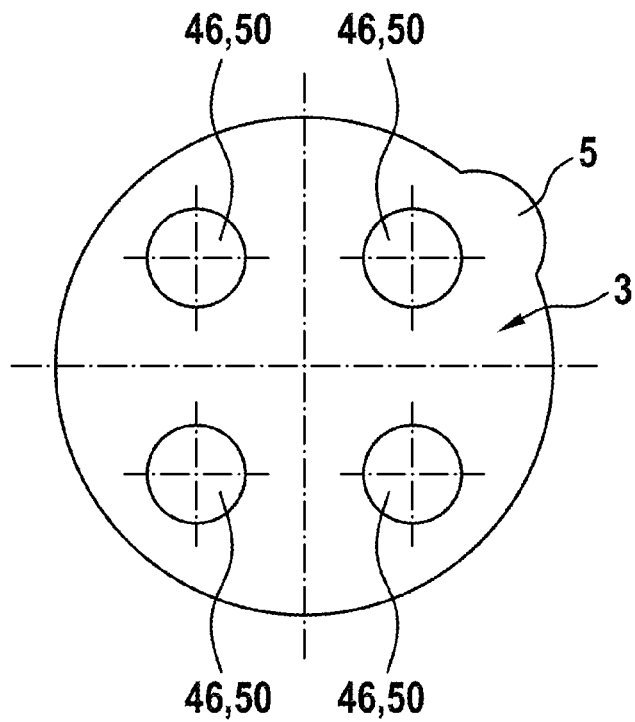
FIG. 3 shows a view explaining the arrangement of suction cups during the removal of a closure lid from a stack of closure elements according to FIG. 2, and FIGS. 4 and 5 each show a simplified view of the region of a gripping mechanism during the freeing of different regions of a closure element.

As can be seen in particular from a comparison of FIGS. 1 to 3, each holding mechanism 25 assigned to a closure element 3 comprises a plurality of holding elements 46 in the form of suction cups 50. For example, as can be seen in particular from FIG. 3, each closure element 3 is assigned four holding elements 46 or suction cups 50, which are arranged for example at corners of an imaginary square inside the closure element 3 having substantially a circular outer contour. FIG. 3 also shows an opening tab 5 on the closure element 3, which opening tab 5 serves to open a closed packaging container 1 and protrudes beyond the circular outer cross section of the closure element 3.

Figure 4:
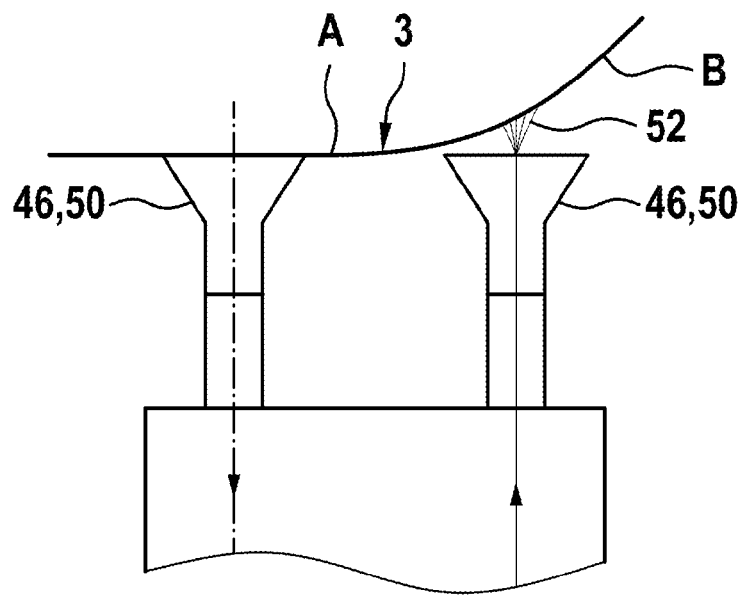

FIGS. 2 and 3 show that, in a position in which the holding mechanism 25 is located in the region of the magazine 30, the holding mechanism 25 has initially been moved radially toward the (lowest) closure element 3 facing it in the magazine 30. By applying a vacuum or underpressure to the holding elements 46 and by moving the holding mechanism 25 radially from the region of the magazine 30, the closure element 3 is then pulled off from the magazine 30. All four holding elements 46 or suction cups 50 are here arranged in operative contact with the closure element 3. During the further conveying of the pulled-off closure element 3 inside the sterile chamber 12, and in order to carry out the process of sterilizing the closure elements 3, the two holding elements 46 or suction cups 50 lying on one side are then first of all deactivated in a first phase, according to the view in FIG. 4, and at the same time hot air 52 at an overpressure is guided in the direction of the closure element 3 through the suction cups 50. The top side B of the closure element 3 thus lifts away from the two last-mentioned suction cups 50, wherein this region can be treated or sterilized by the hot air 52 across the whole surface. During this phase, however, the two other holding elements 46 or suction cups 50 are still arranged in operative connection with the closure element 3 in order to hold the latter precisely in position on the holding mechanism 25.

Figure 5:
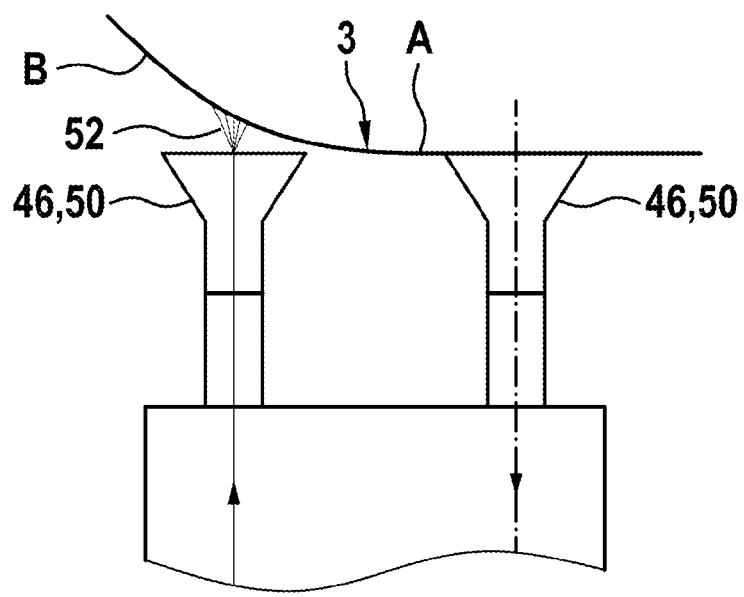

Then, during the further conveying of the closure element 3, the initially inactive suction cups 50 are activated by applying an underpressure and stopping the hot air 52 and by then deactivating the other two suction cups 50 and guiding hot air 52 through the corresponding suction cup 50 according to the view in FIG. 5. By virtue of the successive, alternating holding of the closure elements 3 by means of the suction cups 50 and the temporary freeing of the closure lids 3 in the region of the top sides B, all of the (surface) regions of the closure lids 3 are thus treated completely by the hot air 52, i.e. the undersides A by the hot air 6 by means of the blower nozzles 36, 38, and also the top sides B by the hot air 52, during the first phase of the sterilization.

The closure elements 3 are then conveyed into the region of the sterilizing nozzle 40, where the vaporous sterilizing medium 41 acts on the closure element 3 during a second phase of the sterilization process. Here too, by virtue of alternating holding of the closure element 3 and freeing of the closure elements 3 by the four holding elements 46 or suction cups 50, the vaporous sterilizing medium 41 acts completely on all regions of the closure element 3. Thereafter, the closure element 3 is dried by means of the hot-air nozzle 42 in a third phase of the sterilizing process, and finally, by increasing the radial distance of the holding arm 22 from the rotation axle 16, the closure element 3 is placed onto the opening 4 of the packaging container 1.

After the closure element 3 has been placed onto the opening of the packaging container 1, a heat-sealing station 60 likewise arranged for example in the region of the sterile chamber 12 then ensures that the packaging containers 1 are closed or sealed by means of the closure elements 3.

The above-described method and the device 10 can be modified in many ways without departing from the inventive concept. In particular, the invention is not intended to be limited to thin closure elements 3 in the form of cover films or the like. It is thus also conceivable, for example, that rigid closure elements can be temporarily removed from contact with the closure lids 3 by means of suitably designed holding mechanisms, so that all the surfaces of such a closure lid 3 can be sterilized.

What is claimed is:

1. A method for sterilizing closure elements (3) for packaging containers (1), wherein the closure elements (3) are collected individually by a respective holding mechanism (25) in the region of a sterile chamber (12) and are placed onto an opening (4) of a respective filled packaging container (1) and connected to the packaging container, wherein the closure elements (3), while being conveyed inside the sterile chamber (12), are treated by at least one sterilizing medium (6, 7, 52) during a sterilizing process, and wherein the holding mechanism (25) holds the closure element (3) successively at different locations of the closure element (3) in such a way that, during the sterilizing process, all surfaces (A, B) of the closure element (3) come temporarily into operative connection with at least one sterilizing medium (6, 7, 52),
    wherein the holding mechanism (25) has a plurality of holding elements (46) in the form of suction cups (50) that are configured to contact the closure element (3) and, in order to bring the suction cups (50) out of contact with the closure element (3), a medium at an overpressure acts on the closure element (3) through the suction cups (50).

2. The method according to claim 1, characterized in that the sterilization of the closure elements (3) comprises a first phase in which hot air acts as the at least one sterilizing medium (6, 52) on the closure elements (3), a second phase in which vaporous sterilizing agent acts as the at least one sterilizing medium (7), and a third phase in which the closure elements (3) are dried with hot air, wherein at least during the first and second phases the closure elements (3), in the region of the all surfaces (A, B), come into operative connection with the sterilizing medium (6, 7, 52).

3. The method according to claim 2, wherein the at least one sterilizing medium (7) contains hydrogen peroxide.

4. A device (10) for sterilizing closure elements (3) for packaging containers (1), the device comprising a holding mechanism (25) for holding in each case one closure element (3) in the region of a sterile chamber (12), and a sterilizing mechanism (35) for at least one sterilizing medium (6, 7, 52) for sterilizing the closure elements (3) in the region of the sterile chamber (12), wherein the holding mechanism (25) has a plurality of holding elements (46) for in each case one closure element (3), which holding elements (46) are alternately arranged temporarily out of contact with the closure element (3) in order to allow the at least one sterilizing medium (6, 7, 52) to act on the closure element (3),
    characterized in that the holding elements (46) are configured in the form of suction cups (50) and, in order to bring the suction cups (50) out of contact with the closure element (3), the suction cups (50) are configured such that a medium at an overpressure acts on the closure element (3) through the suction cups (50).

5. The device according to claim 4, characterized in that the medium at an overpressure is hot air.

6. The device according to claim 4, characterized in that a plurality of holding elements (46) assigned to a closure element (3) are arranged simultaneously in holding contact with the closure element (3).

7. The device according to claim 4, characterized in that the holding elements (46) are arranged in a radially protruding manner on a conveying star (20) rotatable about a rotation axle (16) inside the sterile chamber (12).

8. The device according to claim 7, characterized in that the holding elements (46) are arranged radially movably with respect to the rotation axle (16) in order to collect an individual closure element (3) from the closure elements (3), which are stacked on top of each other in a magazine (30), and in order to place the individual closure element (3) onto an opening (4) of a filled packaging container (1).

9. The device according to claim 7, characterized in that, on the conveying path of the closure elements (3) inside the sterile chamber (12), a plurality of sterilizing elements (36, 38, 40) are arranged as part of the sterilizing mechanism (35) for the closure elements (3).

10. The device according to claim 9, characterized in that the sterilizing elements (36, 38, 40) are nozzle-like.

11. The device according to claim 7, wherein a plurality of holding mechanisms (25) are provided each for a respective closure element (3), and wherein the holding mechanisms (25) are arranged on the conveying star (20) at uniform angle distances about the rotation axle (16).

12. A method for sterilizing deformable closure elements (3) in the form of flat closure lids in the region of a filling installation (100) for foods such as yoghurt or the like, the method utilizing the device according to claim 3.

13. A method for sterilizing deformable closure elements (3) in the form of flat closure lids in the region of a filling installation (100) for foods such as yoghurt or the like, the method comprising performing the method according to claim 1.

* * * * *